(12) United States Patent
Wang et al.

(10) Patent No.: US 8,288,564 B2
(45) Date of Patent: Oct. 16, 2012

(54) PROCESS FOR PRODUCING TRANS-DIBENZOXENOPYRROLE COMPOUND AND INTERMEDIATE THEREFOR

(75) Inventors: Weiqi Wang, Toyonaka (JP); Tetsuya Ikemoto, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 55 days.

(21) Appl. No.: 12/667,654

(22) PCT Filed: Jul. 7, 2008

(86) PCT No.: PCT/JP2008/062279
§ 371 (c)(1),
(2), (4) Date: Jan. 4, 2010

(87) PCT Pub. No.: WO2009/008405
PCT Pub. Date: Jan. 15, 2009

(65) Prior Publication Data
US 2011/0046393 A1    Feb. 24, 2011

(30) Foreign Application Priority Data

Jul. 6, 2007 (JP) .................. 2007-178112
Jan. 31, 2008 (JP) .................. 2008-020889

(51) Int. Cl.
C07D 491/22  (2006.01)
(52) U.S. Cl. ....................................... 548/421
(58) Field of Classification Search ............ 548/421
See application file for complete search history.

(56) References Cited

U.S. PATENT DOCUMENTS

| 4,145,434 A | 3/1979 | van der Burg |
| 4,977,158 A | 12/1990 | Wieringa |
| 2009/0227803 A1* | 9/2009 | Kemperman ............... 548/421 |

FOREIGN PATENT DOCUMENTS

| JP | 49-069697 A | 7/1974 |
| JP | 53-002465 A | 1/1978 |
| JP | 02-111776 A | 4/1990 |
| JP | 2007-137877 A | 6/2007 |
| WO | 2006/106136 A1 | 10/2006 |

OTHER PUBLICATIONS

Jan Vader et al., "The Synthesis of Radiolabelled Org 5222 and Its Main Metabolite Org 30526", Journal of Labelled Compounds and Radiopharmaceuticals, 1994, vol. 34, No. 9, pp. 845-869.
"Advanced Organic Chemistry; Reactions, Mechanisms and Structure", 4th edition, John Wiley & Sons, 1992, pp. 898-900.
"Eschweiler-Clark Reductive Alkylation of Amines", Name Reactions for Functional Group Transformations, 1st Edition, John Wiley & Sons, Jul. 2007, pp. 86-87.
"Eschweiler-Clarke (Clark) Methylation", Name Reactions and Reagents in Organic Synthesis, 2nd edition, John Wiley & Sons, Apr. 2005, pp. 232-233.
"Org-5222", Drugs of the Future, 1993, 18(12), pp. 1117-1123.
Communication from the European Patent Office received in corresponding Application No. 08777941.9, dated Nov. 22, 2011.
Wildenberg, H.M.v.d., et al.. "Biotransformation of trans-5-Chloro-2-methyl-2,3,3a,12b-tetrahydro-1H-dibenz[2,3 : 6,7] oxepino [4,5-c] pyrrolidine Maleate in Rats" Drug Res. 1990, 40,pp. 540-544.

* cited by examiner

*Primary Examiner* — Shawquia Young
(74) *Attorney, Agent, or Firm* — Sughrue Mion, PLLC

(57) ABSTRACT

The invention provides a process for production of trans-dibenzoxenopyrrole compounds, in which reduction, leaving group conversion, hydrogenation and methylation are carried out in that order. The process of the invention allows trans-dibenzoxenopyrrole compounds to be produced by a simpler procedure than conventional processes. The invention further provides novel compounds obtained as intermediates in the process, and a process for their production.

11 Claims, No Drawings

PROCESS FOR PRODUCING TRANS-DIBENZOXENOPYRROLE COMPOUND AND INTERMEDIATE THEREFOR

TECHNICAL FIELD

The present invention relates to a process for production of trans-dibenzoxenopyrrole compounds, and to intermediates of the same.

BACKGROUND ART

The known processes for production of trans-dibenzoxenopyrrole compounds include the process represented by the following formula, described in Patent document 1, for example.

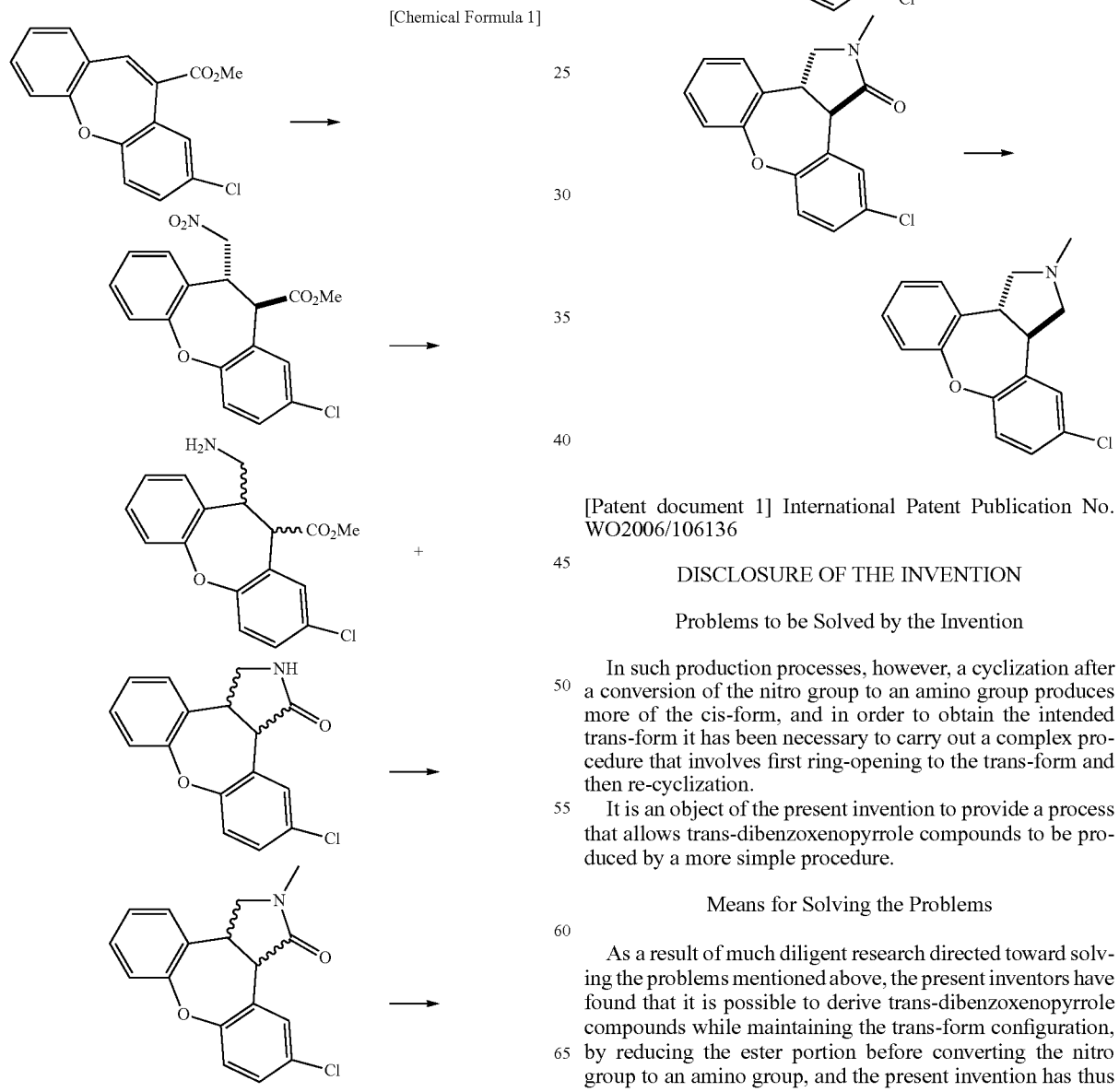

[Chemical Formula 1]

[Patent document 1] International Patent Publication No. WO2006/106136

DISCLOSURE OF THE INVENTION

Problems to be Solved by the Invention

In such production processes, however, a cyclization after a conversion of the nitro group to an amino group produces more of the cis-form, and in order to obtain the intended trans-form it has been necessary to carry out a complex procedure that involves first ring-opening to the trans-form and then re-cyclization.

It is an object of the present invention to provide a process that allows trans-dibenzoxenopyrrole compounds to be produced by a more simple procedure.

Means for Solving the Problems

As a result of much diligent research directed toward solving the problems mentioned above, the present inventors have found that it is possible to derive trans-dibenzoxenopyrrole compounds while maintaining the trans-form configuration, by reducing the ester portion before converting the nitro group to an amino group, and the present invention has thus been completed.

Specifically, the invention provides a process for production of trans-dibenzoxenopyrrole compounds represented by general formula (VI):

[Chemical Formula 2]

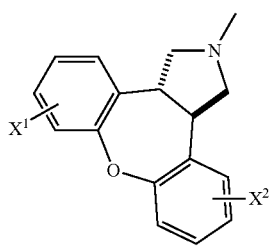
(VI)

[wherein $X^1$ and $X^2$ are the same or different and each independently represents hydrogen or a halogen atom]
or pharmacologically acceptable salts thereof, the process comprising the following steps A-D.

Step A: A step in which a compound represented by general formula (II):

[Chemical Formula 3]

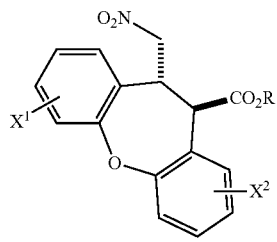
(II)

[wherein R represents an alkyl group optionally substituted with a phenyl group, and $X^1$ and $X^2$ have the same definitions as above]
is reduced to obtain a compound represented by general formula (III):

[Chemical Formula 4]

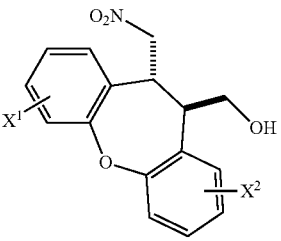
(III)

[wherein $X^1$ and $X^2$ have the same definitions as above].

Step B: A step of leaving group conversion of a compound represented by general formula (III) to obtain a compound represented by general formula (IV):

[Chemical Formula 5]

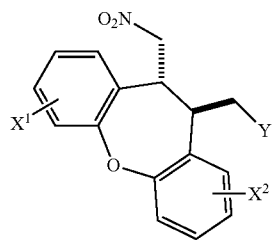
(IV)

[wherein $X^1$ and $X^2$ have the same definitions as above, and Y represents a leaving group].

Step C: A step in which a compound represented by general formula (IV) is subjected to hydrogenation to obtain a trans-dibenzoxenopyrrole compound represented by general formula (V):

[Chemical Formula 6]

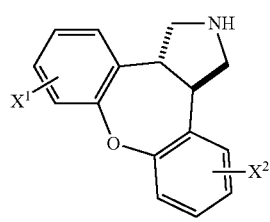
(V)

[wherein $X^1$ and $X^2$ have the same definitions as above].

Step D: A step in which a trans-dibenzoxenopyrrole compound represented by general formula (V) is methylated to obtain a trans-dibenzoxenopyrrole compound represented by general formula (VI).

By this process, a trans-dibenzoxenopyrrole compound can be produced in a more simple manner without the complex procedure of first opening the ring to produce the trans-form and then recyclizing.

The compounds represented by general formulas (III)-(V) obtained as intermediates in the process described above are novel compounds discovered by the present inventors during the course of devising the present invention. Specifically, the invention provides the following compounds and processes.

Compounds Represented by General Formula (III).
  A process for production of a compound represented by general formula (III), the process comprising step A (a step in which a compound represented by general formula (II) is reduced to obtain a compound represented by general formula (III)).
Compounds Represented by General Formula (IV).
  A process for production of a compound represented by general formula (IV), the process comprising step B (a step of leaving group conversion of a compound represented by general formula (III) to obtain a compound represented by general formula (IV)).
trans-Dibenzoxenopyrrole compounds represented by general formula (V).
  A process for production of a trans-dibenzoxenopyrrole compound represented by general formula (V), the process comprising step C (a step in which a compound represented by general formula (IV) is subjected to hydrogenation to obtain a trans-dibenzoxenopyrrole compound represented by general formula (V)).

A process for production of a trans-dibenzoxenopyrrole compound represented by general formula (VI), the process comprising step D: (a step in which a trans-dibenzoxenopyrrole compound represented by general formula (V) is methylated to obtain a trans-dibenzoxenopyrrole compound represented by general formula (VI)).

EFFECT OF THE INVENTION

According to the invention there is provided an industrially advantageous process that allows trans-dibenzoxenopyrrole compounds to be produced by a simpler procedure than the known processes.

BEST MODES FOR CARRYING OUT THE INVENTION

Preferred embodiments of the invention will now be described in detail.

The process of the invention for production of trans-dibenzoxenopyrrole compounds represented by general formula (VI) or their pharmacologically acceptable salts comprises steps A to D.

(Step A)

Step A, which is the step of reducing a compound represented by general formula (II) (hereinafter abbreviated as "compound (II)") to obtain a compound represented by general formula (III) (hereinafter abbreviated as "compound (III)") will be explained first. The compounds of (III) are novel compounds.

As examples of alkyl groups represented by R in general formula (II) there may be mentioned C1-6 alkyl groups such as methyl, ethyl, propyl, isopropyl, butyl, isobutyl, tert-butyl, pentyl and hexyl. As examples of alkyl groups substituted with phenyl groups there may be mentioned benzyl, 1-phenylethyl and 2-phenylethyl. R is most preferably a methyl or ethyl group from the viewpoint of facilitating synthesis of compound (II).

As halogen atoms represented by $X^1$ and $X^2$ there may be mentioned fluorine, chlorine, bromine and iodine, with chlorine being preferred. Carrying out steps A-D can yield a compound or salt with higher pharmacological activity (a trans-dibenzoxenopyrrole compound represented by general formula (VI) or its salt), and therefore one of $X^1$ and $X^2$ is preferably hydrogen while the other is chlorine.

As examples for compound (II) there may be mentioned trans-8-chloro-11-(nitromethyl)-10,11-dihydrodibenzo[b,f]oxepin-10-carboxylic acid esters such as methyl trans-8-chloro-11-(nitromethyl)-10,11-dihydrodibenzo[b,f]oxepin-10-carboxylate, ethyl trans-8-chloro-11-(nitromethyl)-10,11-dihydrodibenzo[b,f]oxepin-10-carboxylate, propyl trans-8-chloro-11-(nitromethyl)-10,11-dihydrodibenzo[b,f]oxepin-10-carboxylate, isopropyl trans-8-chloro-11-(nitromethyl)-10,11-dihydrodibenzo[b,f]oxepin-10-carboxylate and tert-butyl trans-8-chloro-11-(nitromethyl)-10,11-dihydrodibenzo[b,f]oxepin-10-carboxylate; trans-2-chloro-11-(nitromethyl)-10,11-dihydrodibenzo[b,f]oxepin-10-carboxylic acid esters such as methyl trans-2-chloro-11-(nitromethyl)-10,11-dihydrodibenzo[b,f]oxepin-10-carboxylate, ethyl trans-2-chloro-11-(nitromethyl)-10,11-dihydrodibenzo[b,f]oxepin-10-carboxylate, propyl trans-2-chloro-11-(nitromethyl)-10,11-dihydrodibenzo[b,f]oxepin-10-carboxylate, isopropyl trans-2-chloro-11-(nitromethyl)-10,11-dihydrodibenzo[b,f]oxepin-10-carboxylate and tert-butyl trans-2-chloro-11-(nitromethyl)-10,11-dihydrodibenzo[b,f]oxepin-10-carboxylate; trans-2,8-dichloro-11-(nitromethyl)-10,11-dihydrodibenzo[b,f]oxepin-10-carboxylic acid esters such as methyl trans-2,8-dichloro-11-(nitromethyl)-10,11-dihydrodibenzo[b,f]oxepin-10-carboxylate; and trans-11-(nitromethyl)-10,11-dihydrodibenzo[b,f]oxepin-10-carboxylic acid esters such as methyl trans-11-(nitromethyl)-10,11-dihydrodibenzo[b,f]oxepin-10-carboxylate; as well as these compounds with "chloro" replaced by "fluoro", "bromo" or "iodo". From the viewpoint of facilitating synthesis and increasing the pharmacological activity of the compound or salt obtained by steps A-D, compound (II) is most preferably methyl trans-2-chloro-11-(nitromethyl)-10,11-dihydrodibenzo[b,f]oxepin-10-carboxylate or ethyl trans-2-chloro-11-(nitromethyl)-10,11-dihydrodibenzo[b,f]oxepin-10-carboxylate.

Compound (II) may be produced by a known process whereby, for example, a compound represented by general formula (I):

[Chemical Formula 7]

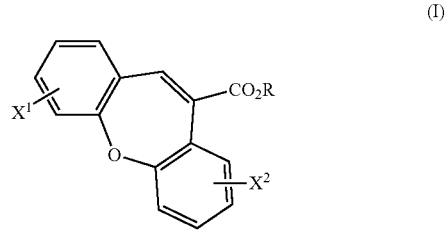

(I)

[wherein R, $X^1$ and $X^2$ have the same definitions as above] (hereinafter referred to as "compound (I)") is reacted with nitromethane (see International Patent Publication No. 2006/106136, for example).

The reducing agent used for reduction in this step may be any one that preferentially reduces ester groups over nitro groups, and boron hydride compounds or aluminum hydride compounds can be used in most cases. As examples of boron hydride compounds there may be mentioned alkali metal borohydrides such as lithium borohydride, sodium borohydride and potassium borohydride; and borane compounds such as diborane and borane. As examples of aluminum hydride compounds there may be mentioned lithium aluminum hydride, sodium bis(2-methoxyethoxy)aluminum hydride, lithium tri-tert-butoxyaluminum hydride and aluminum hydride. From the viewpoint of further increasing the reduction selectivity for ester groups, the reducing agent is preferably a borohydride compound and more preferably borane or sodium borohydride. In most cases, borane may be used as a complex with tetrahydrofuran, diethyl ether or the like. The amount of reducing agent used will usually be 1-10 mol and preferably 1-3 mol with respect to 1 mol of compound (II).

When an alkali metal borohydride is used as the reducing agent, a Lewis acid such as boron trifluoride, a Bronsted acid such as sulfuric acid or a dialkyl sulfate such as dimethyl sulfate may also be used as an additional reducing agent. Using boron trifluoride, sulfuric acid, dimethyl sulfate or the like as an additional reducing agent will further increase the yield of compound (III). The amount used will usually be 1-3 mol and preferably 1-1.5 mol with respect to 1 mol of the alkali metal borohydride. From the viewpoint of further increasing the reduction selectivity for ester groups and the yield of compound (III), a Lewis acid is more preferred and boron trifluoride is even more preferred as the additional reducing agent. In most cases, boron trifluoride can be used as a complex with tetrahydrofuran or the like.

The reduction will usually be carried out in the presence of a solvent. The solvent is not particularly restricted so long as it does not interfere with the reaction, and as examples there may be mentioned ether solvents such as diethyl ether, tert-butyl methyl ether, 1,2-dimethoxyethane, cyclopentyl methyl ether, diglyme and tetrahydrofuran, with tetrahydrofuran being preferred. The amount of solvent used will usually be 1-100 L and preferably 3-30 L to 1 kg of compound (II).

The reaction temperature for reduction will normally be 0° C.-100° C. and preferably 30° C.-60° C. Progress of the reaction can be confirmed by ordinary means such as gas chromatography or high-performance liquid chromatography. The reaction time will normally be 1-24 hours and preferably 3-10 hours.

The reduction is carried out by mixing compound (II) and the reducing agent, with no particular restriction on the order of mixing. Preferred modes include adding the reducing agent to a mixture of compound (II) and a solvent, and adding a mixture of compound (II) and a solvent to a mixture of the reducing agent and a solvent. When an alkali metal borohydride is used as the reducing agent, a more preferred mode is one wherein a mixture of compound (II) and a solvent is added to a mixture of the alkali metal borohydride and a solvent, and then a Lewis acid, Bronsted acid or dialkyl sulfate is added thereto, or one wherein a Lewis acid, Bronsted acid or dialkyl sulfate is added to a mixture of the alkali metal borohydride and a solvent and then a mixture of compound (II) and a solvent is added thereto.

The mixture obtained upon completion of the reduction contains compound (III), and this mixture may be supplied directly to step B, although usually it will be supplied to step B after post-treatment such as washing and extraction. Compound (III) may also be isolated by ordinary isolating treatment of the mixture or its treated product by concentration, crystallization or the like, for example, before being supplied to step B. The isolated compound (III) may be supplied to step B after purification by ordinary purification means such as recrystallization or column chromatography.

As examples of compound (III) obtained in this manner there may be mentioned trans-[8-chloro-11-(nitromethyl)-10,11-dihydrodibenzo[b,f]oxepin-10-yl]methanol, trans-[2-chloro-11-(nitromethyl)-10,11-dihydrodibenzo[b,f]oxepin-10-yl]methanol, trans-[2,8-dichloro-11-(nitromethyl)-10,11-dihydrodibenzo[b,f]oxepin-10-yl]methanol and trans-[11-(nitromethyl)-10,11-dihydrodibenzo[b,f]oxepin-10-yl]methanol, as well as these compounds with "chloro" replaced by "fluoro", "bromo" or "iodo".

(Step B)

Step B, which is the step of leaving group conversion of compound (III) to obtain a compound represented by general formula (IV) (hereinafter abbreviated as "compound (IV)") will be explained next. The compounds of (IV) are novel compounds.

According to the invention, leaving group conversion means reaction wherein the hydroxyl of compound (III) is converted to the leaving group represented by Y.

The leaving group represented by Y may be, for example, a halogen atom such as chlorine, bromine or iodine; a C1-6 alkanesulfonyloxy group such as methanesulfonyloxy, ethanesulfonyloxy or hexanesulfonyloxy; a C1-6 perfluoroalkanesulfonyloxy group such as trifluoromethanesulfonyloxy, pentafluoroethanesulfonyloxy or perfluorohexanesulfonyloxy; or a benzenesulfonyloxy group such as benzenesulfonyloxy, para-toluenesulfonyloxy or 4-trifluoromethylbenzenesulfonyloxy (where the benzenesulfonyloxy group is optionally substituted on the benzene ring with a C1-6 alkyl group or C1-6 perfluoroalkyl group). From the viewpoint of further increasing the yield of compound (V) in step C following this step, Y is preferably a halogen atom or C1-6 alkanesulfonyloxy group, more preferably chlorine, bromine or a methanesulfonyloxy group, and even more preferably a methanesulfonyloxy group.

A halogenating agent or sulfonating agent can usually be used for the leaving group conversion in this step. As examples of halogenating agents there may be mentioned chlorinating agents such as phosphorus pentachloride, phosphorus trichloride, phosphorus oxychloride and thionyl chloride, and brominating agents such as phosphorus tribromide and thionyl bromide. As examples of sulfonating agents there may be mentioned C1-6 alkanesulfonyl chlorides such as methanesulfonyl chloride, ethanesulfonyl chloride and hexanesulfonyl chloride; C2-12 alkanesulfonic anhydrides such as methanesulfonic anhydride, ethanesulfonic anhydride and hexanesulfonic anhydride; C1-6 perfluoroalkanesulfonyl chlorides such as trifluoromethanesulfonyl chloride, pentafluoroethanesulfonyl chloride and perfluorohexanesulfonyl chloride; C2-12 perfluoroalkanesulfonic anhydrides such as trifluoromethanesulfonic anhydride, pentafluoroethanesulfonic anhydride and perfluorohexanesulfonic anhydride; benzenesulfonyl chlorides such as benzenesulfonyl chloride, para-toluenesulfonyl chloride and 4-trifluoromethylbenzenesulfonyl chloride (where the benzenesulfonyl chloride is optionally substituted on the benzene ring with a C1-6 alkyl group or C1-6 perfluoroalkyl group); and benzenesulfonic anhydrides such as benzenesulfonic anhydride and para-toluenesulfonic anhydride (where the benzenesulfonic anhydride is optionally substituted on the benzene ring with a C1-6 alkyl group or C1-6 perfluoroalkyl group). From the viewpoint of further increasing the yield of compound (V) in step C following this step, the leaving group conversion reagent (halogenating agent, sulfonating agent or the like) is preferably a C1-6 alkanesulfonyl chloride and more preferably methanesulfonyl chloride. The amount of leaving group conversion reagent used will usually be 1-5 mol and preferably 1-3 mol with respect to 1 mol of compound (III).

The leaving group conversion is preferably carried out in the presence of a base. As examples for the base there may be mentioned tertiary amines such as trimethylamine, triethylamine, diisopropylethylamine, tributylamine, N-methylmorpholine and 1,4-diazabicyclo[2.2.2]octane; aromatic amines such as pyridine, 2-methyl-5-ethylpyridine, 2,6-di-tert-butylpyridine, 4-dimethylaminopyridine, imidazole and 1-methylimidazole; and cyclic amidines such as 1,8-diazabicyclo[5.4.0]-7-undecene and 1,5-diazabicyclo[4.3.0]-5-nonene. Tertiary amines are preferred, with triethylamine being more preferred. The amount of base used will usually be 1-5 mol and preferably 1-3 mol with respect to 1 mol of compound (III).

The leaving group conversion will usually be carried out in the presence of a solvent. The solvent is not particularly restricted so long as it does not interfere with the reaction, and as examples there may be mentioned ether solvents such as diethyl ether, tert-butyl methyl ether, cyclopentyl methyl ether, 1,2-dimethoxyethane, diglyme and tetrahydrofuran; and aromatic hydrocarbon solvents such as toluene, xylene, chlorobenzene and nitrobenzene. These solvents may be used alone, or two or more may be used simultaneously. Tetrahydrofuran and toluene are preferred. The amount of solvent used will usually be 1-100 L and preferably 3-30 L to 1 kg of compound (III).

The reaction temperature for leaving group conversion will normally be −30° C. to 80° C. and preferably −10° C. to 30° C. Progress of the reaction can be confirmed by ordinary means such as gas chromatography or high-performance liquid chromatography.

The leaving group conversion is accomplished by mixing compound (III) and the leaving group conversion reagent (halogenating agent, sulfonating agent or the like) in the presence or in the absence of a base, and the order of mixing is not particularly restricted. As a preferred mode there may be mentioned a mode in which the leaving group conversion reagent is added to a mixture of compound (III) and a base.

The mixture obtained upon completion of the leaving group conversion contains compound (IV), and this mixture may be supplied directly to step C, although usually it will be supplied to step C after post-treatment such as washing and extraction. Compound (IV) may also be isolated by ordinary isolating treatment of the mixture or its treated product by concentration, crystallization or the like, for example, before being supplied to step C. The isolated compound (IV) may be supplied to step C after purification by ordinary purification means such as recrystallization or column chromatography.

As examples for compound (IV) obtained in this manner there may be mentioned trans-[8-chloro-11-(nitromethyl)-10,11-dihydrodibenzo[b,f]oxepin-10-yl]methyl methanesulfonate, trans-[8-chloro-11-(nitromethyl)-10,11-dihydrodibenzo[b,f]oxepin-10-yl]methyl ethane sulfonate, trans-[8-chloro-11-(nitromethyl)-10,11-dihydrodibenzo[b,f]oxepin-10-yl]methyl trifluoromethanesulfonate, trans-[8-chloro-11-(nitromethyl)-10,11-dihydrodibenzo[b,f]oxepin-10-yl] methyl pentafluoroethane sulfonate, trans-[8-chloro-11-(nitromethyl)-10,11-dihydrodibenzo[b,f]oxepin-10-yl] methyl benzene sulfonate, trans-[8-chloro-11-(nitromethyl)-10,11-dihydrodibenzo[b,f]oxepin-10-yl]methyl para-toluene sulfonate, trans-[8-chloro-11-(nitromethyl)-10,11-dihydrodibenzo[b,f]oxepin-10-yl]methyl chloride, trans-[8-chloro-11-(nitromethyl)-10,11-dihydrodibenzo[b,f]oxepin-10-yl]methyl bromide, 8-chloro-11-(nitromethyl)-10,11-dihydrodibenzo[b,f]oxepin-10-yl]methyl iodide, trans-[2-chloro-11-(nitromethyl)-10,11-dihydrodibenzo[b,f]oxepin-10-yl]methyl methanesulfonate, trans-[2,8-dichloro-11-(nitromethyl)-10,11-dihydrodibenzo[b,f]oxepin-10-yl] methyl methanesulfonate and trans-[11-(nitromethyl)-10,11-dihydrodibenzo[b,f]oxepin-10-yl]methyl methanesulfonate; as well as these compounds with "chloro" replaced by "fluoro", "bromo" or "iodo".

When the reaction yields a compound of general formula (IV) wherein Y is a C1-6 alkanesulfonyloxy, C1-6 perfluoroalkanesulfonyloxy or benzenesulfonyloxy group (the benzenesulfonyloxy group being optionally substituted on the benzene ring with a C1-6 alkyl group or C1-6 perfluoroalkyl group) (hereinafter also abbreviated as "sulfonyl compound (IV)"), this step may further include a reaction in which the sulfonyl compound (IV) and an alkali metal halide are reacted to obtain a compound of general formula (IV) wherein Y is a halogen atom (hereinafter also abbreviated as "halogenated compound (IV)") (hereinafter, this will also be referred to simply as "halogenation").

As examples of alkali metal halides there may be mentioned lithium chloride, lithium bromide, sodium bromide, sodium iodide and potassium iodide. The amount of alkali metal halide used will normally be 1-20 mol and preferably 1-5 mol with respect to 1 mol of the sulfonyl compound (IV).

The halogenation will usually be carried out in the presence of a solvent. The solvent is not particularly restricted so long as it does not interfere with the reaction, and as examples there may be mentioned ketone solvents such as acetone, methyl ethyl ketone, methyl isobutyl ketone; and ester solvents such as ethyl acetate and isopropyl acetate. These solvents may be used alone, or two or more may be used simultaneously. The amount of solvent used will normally be 1-50 L and preferably 3-20 L to 1 kg of the sulfonyl compound (IV).

The reaction temperature for the halogenation will normally be 20° C.-100° C. and preferably 40° C.-80° C. Progress of the reaction can be confirmed by ordinary means such as gas chromatography or high-performance liquid chromatography.

The halogenation is accomplished by mixing the sulfonyl compound (IV) and alkali metal halide, with no particular restriction on the order of mixing.

The compounds obtained upon completion of the halogenation include the halogenated compound (IV), and this mixture may be supplied directly to step C, although usually it will be supplied to step C after post-treatment such as washing and extraction. The halogenated compound (IV) may also be isolated by ordinary isolating treatment of the mixture or its treated product by concentration, crystallization or the like, for example, before being supplied to step C. The isolated halogenated compound (IV) may be supplied to step C after purification by ordinary purification means such as recrystallization or column chromatography.

(Step C)

Step C, which is a step of hydrogenation of compound (IV) to obtain a trans-dibenzoxenopyrrole compound represented by general formula (V) (hereinafter abbreviated as "compound (V)"), will be explained next. The compounds of (V) are novel compounds.

The hydrogenation in this step is accomplished by any mode such as allowing compound (IV) to contact with hydrogen in the presence of a catalyst, or mixing compound (IV) with a hydrogen-donating reagent (the hydrogen source reagent) in the presence of a catalyst. A preferred mode is the mode of allowing compound (IV) to contact with hydrogen in the presence of a catalyst.

As examples of catalysts there may be mentioned metal catalysts or metal compound catalysts containing elements of Group 9 or Group 10 of the Periodic Table, such as sponge nickel, sponge cobalt, palladium/carbon, palladium hydroxide, platinum/carbon, platinum oxide and the like. Sponge nickel is preferred. The amount of catalyst used will normally be 0.001-10 kg and preferably 0.01-0.5 kg to 1 kg of compound (IV).

The hydrogen used may be commercially available hydrogen gas in most cases. Contact of compound (IV) and hydrogen gas may be accomplished, for example, by circulating through the gas phase section of a reactor, bubbling through the reaction mixture, or pressure charging hydrogen in a pressure-resistant container. The amount of hydrogen used is not particularly restricted so long as it is at least 1 mol with respect to 1 mol of compound (IV). The hydrogen pressure in the reaction system is usually 0.1-2 MPa and preferably 0.1-1 MPa.

The hydrogen-donating reagent may be formic acid, for example. The amount used is not particularly restricted so long as it is at least 1 mol with respect to 1 mol of compound (IV), and it will usually be 0.5-50 kg to 1 kg of compound (IV).

The hydrogenation will usually be carried out in the presence of a solvent. As examples of solvents there may be mentioned ester solvents such as ethyl acetate, propyl acetate, isopropyl acetate, butyl acetate, isobutyl acetate, tert-butyl acetate, ethyl propionate, propyl propionate and butyl propionate; ether solvents such as diethyl ether, tert-butyl methyl ether, 1,2-dimethoxyethane, diglyme and tetrahydrofuran; alcohol solvents such as methanol, ethanol, 1-propanol, 2-propanol, 1-butanol and 2-butanol; and carboxylic acid solvents such as acetic acid and propionic acid; and water. These solvents may be used alone, or two or more may be used simultaneously. Alcohol solvents are preferred, with methanol, ethanol and 2-propanol being more preferred. The amount of solvent used will usually be 1-100 L and preferably 3-30 L to 1 kg of compound (IV).

The reaction temperature for hydrogenation will normally be −20° C. to 80° C. and preferably 20° C. to 70° C. Progress of the reaction can be confirmed by ordinary means such as gas chromatography or high-performance liquid chromatography.

The mixture obtained upon completion of the hydrogenation normally contains compound (V) as the main product, and this mixture may be supplied directly to step D, although usually it will be supplied to step D after post-treatment such as filtration, neutralization, washing and extraction. Compound (V) may also be isolated by ordinary isolating treatment of the mixture or its treated product by concentration, crystallization or the like, for example, before being supplied to step D. Compound (V) may also be supplied to step D as an acid addition salt. The isolated compound (V) or its acid addition salt may be supplied to step D after purification by ordinary purification means such as recrystallization or column chromatography.

When the mixture after completion of the hydrogenation contains a compound represented by general formula (V'):

[Chemical Formula 8]

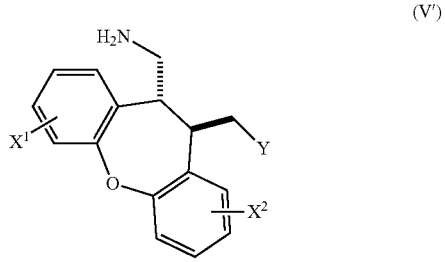

(V')

[wherein $X^1$, $X^2$ and Y have the same definitions as above] (hereinafter abbreviated as "compound (V')"), compound (V') may be cyclized to derive compound (V), by further allowing compound (V') to contact with a base, as necessary.

The base used for cyclization may be an inorganic base or an organic base. As examples of inorganic bases there may be mentioned alkali metal hydroxides such as lithium hydroxide, sodium hydroxide, potassium hydroxide and cesium hydroxide; alkali metal carbonates such as lithium carbonate, sodium carbonate, potassium carbonate and cesium carbonate; alkali metal hydrogencarbonates such as sodium hydrogencarbonate and potassium hydrogencarbonate; alkali metal hydrides such as lithium hydride, sodium hydride and potassium hydride; ammonia; ammonium carbonate; and the like. As examples of organic bases there may be mentioned tertiary amines such as trimethylamine, triethylamine, diisopropylethylamine, tributylamine, N-methylmorpholine and 1,4-diazabicyclo[2.2.2]octane; aromatic amines such as pyridine, 2-methyl-5-ethylpyridine, 2,6-di-tert-butylpyridine, 4-dimethylaminopyridine, imidazole and 1-methylimidazole; cyclic amidines such as 1,8-diazabicyclo[5.4.0]-7-undecene and 1,5-diazabicyclo[4.3.0]-5-nonene; alkali metal alkoxides such as lithium methoxide, sodium methoxide, potassium methoxide, lithium ethoxide, sodium ethoxide, potassium ethoxide and lithium tert-butoxide; and alkali metal amides such as lithium diisopropylamide, lithium hexamethyldisilazide and potassium hexamethyldisilazide. Inorganic bases are preferred, alkali metal carbonates are more preferred and potassium carbonate is even more preferred. The amount of base used will usually be 0.1-20 mol and preferably 1-5 mol with respect to 1 mol of compound (V').

The cyclization will usually be carried out in the presence of a solvent. The solvent is not particularly restricted so long as it does not interfere with the reaction, and as examples there may be mentioned ether solvents such as diethyl ether, tert-butyl methyl ether, cyclopentyl methyl ether, 1,2-dimethoxyethane, diglyme and tetrahydrofuran; amide solvents such as N,N-dimethylformamide, N,N-dimethylacetylamide, N-methylpyrrolidone and 1,3-dimethyl-2-imidazolidinone; ketone solvents such as methyl isobutyl ketone, methyl ethyl ketone, cyclohexanone and cyclopentanone; nitrile solvents such as acetonitrile and propionitrile; alcohol solvents such as methanol, ethanol, 1-propanol, 2-propanol, 1-butanol and 2-butanol; halogen solvents such as methylene chloride and chloroform; and aromatic hydrocarbon solvents such as toluene, xylene, chlorobenzene and nitrobenzene. These solvents may be used alone, or two or more may be used simultaneously. Ether solvents and aromatic hydrocarbon solvents are preferred, with tetrahydrofuran and toluene being more preferred. The amount of solvent used will usually be 1-50 L and preferably 3-20 L to 1 kg of compound (V').

The reaction temperature for cyclization will normally be 0° C.-120° C. and preferably 20° C.-80° C. Progress of the reaction can be confirmed by ordinary means such as gas chromatography or high-performance liquid chromatography.

The cyclization is carried out by mixing compound (V') and the base, with no particular restriction on the order of mixing.

The mixture obtained upon completion of the cyclization contains compound (V), and this mixture may be supplied directly to step D, although usually it will be supplied to step D after post-treatment such as filtration, neutralization, washing and extraction. Compound (V) may also be isolated by ordinary isolating treatment of the mixture or its treated product by concentration, crystallization or the like, for example, before being supplied to step D. Compound (V) may also be supplied to step D as an acid addition salt. The isolated compound (V) or its acid addition salt may be supplied to step D after purification by ordinary purification means such as recrystallization or column chromatography.

The acid used to obtain an acid addition salt of compound (V) may be, for example, an organic acid such as oxalic acid, fumaric acid, maleic acid, succinic acid, adipic acid, malic acid, citric acid, acetic acid, lactic acid, tartaric acid, 2,3-dibenzoyltartaric acid, 2,3-ditoluoyltartaric acid, mandelic acid, benzoic acid, 4-nitrobenzoic acid, 3,5-dinitrobenzoic acid, benzenesulfonic acid, para-toluenesulfonic acid or camphorsulfonic acid; or an inorganic acid such as hydrochloric acid, hydrobromic acid, sulfuric acid, phosphoric acid or nitric acid.

As examples of compound (V) obtained in this manner there may be mentioned trans-5-chloro-2,3,3a,12b-tetrahydro-1H-dibenzo[2,3;6,7]-oxepino[4,5-c]pyrrole, trans-5,11-dichloro-2,3,3a,12b-tetrahydro-1H-dibenzo[2,3;6,7]-oxepino[4,5-c]pyrrole and trans-2,3,3a,12b-tetrahydro-1H-dibenzo[2,3;6,7]-oxepino[4,5-c]pyrrole, as well as these compounds with "chloro" replaced by "fluoro", "bromo" or "iodo".

(Step D)
Finally, Step D, which is a step of methylating compound (VI) to obtain a trans-dibenzoxenopyrrole compound represented by general formula (VI) (hereinafter abbreviated as "compound (VI)"), will now be explained.

The methylation in this step is carried out by reacting compound (V) with an ordinary methylating agent such as a methyl halide (for example, methyl chloride, methyl bromide or methyl iodide), dimethyl sulfate or the like. However, since by-products such as quaternary ammonium salts are produced in the reaction, it is usually carried out using formaldehyde as the methyl source. A formaldehyde aqueous solution (in formalin, for example) may be used to supply formaldehyde to the reaction, or a compound that can generate formaldehyde (such as dimethoxymethane, methoxymethanol, ethoxyethanol, propoxyethanol, butoxyethanol, paraformaldehyde or trioxane) may be used, but preferably formalin is used. The amount of formaldehyde used will usually be 1-20 mol and preferably 2-8 mol with respect to 1 mol of compound (V).

The methylation will usually be carried out using a hydrogen-donating reagent (a reagent that can serve as a hydrogen source) as well. The hydrogen-donating reagent may be formic acid, for example. The amount of hydrogen-donating reagent used will usually be 1-20 mol and preferably 2-8 mol with respect to 1 mol of compound (V).

The methylation will usually be carried out in the presence of a solvent. As examples of solvents there may be mentioned ether solvents such as diethyl ether, tert-butyl methyl ether, cyclopentyl methyl ether, 1,2-dimethoxyethane, diglyme and tetrahydrofuran; nitrile solvents such as acetonitrile and propionitrile; alcohol solvents such as methanol, ethanol, 1-propanol, 2-propanol, 1-butanol and 2-butanol; halogen solvents such as methylene chloride and chloroform; aromatic hydrocarbon solvents such as toluene, xylene, chlorobenzene and nitrobenzene; and water. These solvents may be used alone, or two or more may be used simultaneously. Ether solvents and aromatic hydrocarbon solvents are preferred, with tetrahydrofuran and toluene being more preferred. The amount of solvent used will usually be 1-100 L and preferably 3-30 L to 1 kg of compound (V).

The reaction temperature for the methylation will normally be 0° C.-150° C. and preferably 40° C.-100° C. Progress of the reaction can be confirmed by ordinary means such as gas chromatography or high-performance liquid chromatography. The reaction time will normally be 0.1-12 hours and preferably 0.5-3 hours.

The methylation will usually be carried out by mixing compound (V) with formaldehyde or a compound that generates it, and a hydrogen-donating reagent, with no particular restriction on the order of mixing. As a preferred mode there may be mentioned a mode in which a mixture of formalin and the hydrogen-donating reagent is added to compound (V).

The mixture obtained upon completion of the methylation contains compound (VI), and if necessary, the mixture may be subjected to ordinary post-treatment such as filtration, neutralization, washing and extraction, followed by ordinary isolating treatment such as concentration and crystallization, for isolation of compound (VI). Compound (VI) may also be isolated as an acid addition salt. The isolated compound (VI) or its acid addition salt may be purified by ordinary purification means such as recrystallization or column chromatography.

The acid used to obtain an acid addition salt of compound (VI) may be, for example, an organic acid such as oxalic acid, fumaric acid, maleic acid, succinic acid, adipic acid, malic acid, citric acid, acetic acid, lactic acid, tartaric acid, 2,3-dibenzoyltartaric acid, 2,3-ditoluoyltartaric acid, mandelic acid, benzoic acid, 4-nitrobenzoic acid, 3,5-dinitrobenzoic acid, benzenesulfonic acid, para-toluenesulfonic acid or camphorsulfonic acid; or an inorganic acid such as hydrochloric acid, hydrobromic acid, sulfuric acid, phosphoric acid or nitric acid.

As examples of compound (VI) obtained in this manner there may be mentioned trans-5-chloro-2,3,3a,12b-tetrahydro-2-methyl-1H-dibenzo[2,3;6,7]-oxepino[4,5-c]pyrrole, trans-5,11-dichloro-2,3,3a,12b-tetrahydro-2-methyl-1H-dibenzo[2,3;6,7]-oxepino[4,5-c]pyrrole and trans-2,3,3a,12b-tetrahydro-2-methyl-1H-dibenzo[2,3;6,7]-oxepino[4,5-c]pyrrole, as well as these compounds with "chloro" replaced by "fluoro", "bromo" or "iodo".

As examples of pharmacologically acceptable salts of compound (VI) there may be mentioned carboxylic acid salts such as maleic acid salts, fumaric acid salts and oxalic acid salts; mineral acid salts such as hydrochlorides, hydrobromides and sulfates; and sulfonates such as methanesulfonates (see, for example, Nagase, H., "Saishin Soyaku Kagaku [Recent Innovative Drug Chemistry] Vol. II, Technomics, Inc. (1999) p. 349). Carboxylic acid salts are preferred, with maleic acid salts being particularly preferred.

EXAMPLES

The present invention will now be explained in greater detail based on examples. However, the present invention is not limited to the examples described below.

The compositions of the products in the following examples, production examples and reference examples were all determined by the high-performance liquid chromatographic area percent method. The analysis conditions were as follows.

<Analysis Conditions>
Temperature: 35° C.
Column. Intersil ODS-2 (4.6 mm×150 mm)
Moving bed: Solution A: water (0.1% TFA); solution B: acetonitrile Solvent composition: The proportion of solution B in the solvent was increased from 20% to 70% over 20 minutes, and kept at 70% for 5 minutes.
Flow rate: 1 mL/min
Detector: UV (220 nm)

Reference Example 1

Synthesis of methyl trans-8-chloro-11-(nitromethyl)-10,11-dihydrodibenzo[b,f]oxepin-10-carboxylate (compound (II), R=methyl group)

A mixture of 2.82 g (18.3 mmol) of 1,8-diazabicyclo[5.4.0]-7-undecene and 70 mL of nitromethane was cooled to 11° C., and 35.0 g (122 mmol) of methyl(E)-8-chlorodibenzo[b,f]oxepin-10-carboxylate was added thereto. After stirring the obtained mixture at the same temperature for approximately 14 hours, 1.88 g (12.2 mmol) of 1,8-diazabicyclo[5.4.0]-7-undecene was added in 3 portions every approximately 3 hours at 7-15° C., and stirred therewith. Upon completion of the reaction, the full amount of the obtained reaction mixture was added dropwise to a mixture of 50 mL of 5 wt % hydrochloric acid water and 105 mL of toluene, and then liquid separation was performed to obtain an organic layer. The aqueous layer was also extracted with 35 mL of toluene, and the obtained organic layer was combined with the previously obtained organic layer and the mixture was washed once with 50 mL of 5 wt % hydrochloric acid water and then twice with 50 mL of brine. The obtained organic layer was subjected to dehydration treatment with anhydrous magnesium sulfate and the treated organic layer was concentrated to obtain 45.1 g of a brown solid containing methyl trans-8-chloro-11-(nitromethyl)-10,11-dihydrodibenzo[b,f]oxepin-10-carboxylate.

Composition: trans-form: 87.5%; cis-form: 10.9%.

Example 1

Synthesis of trans-[8-chloro-11-(nitromethyl)-10,11-dihydrodibenzo[b,f]oxepin-10-yl]methanol (compound (III)) (step A)

After mixing 45.1 g of the brown solid containing methyl trans-8-chloro-11-(nitromethyl)-10,11-dihydrodibenzo[b,f]oxepin-10-carboxylate obtained in Reference Example 1 with 170 mL of tetrahydrofuran, 9.23 g (244 mmol) of sodium borohydride powder was added thereto. To the obtained mixture there was added 47.3 g (45.5 wt %, 317 mmol) of a tetrahydrofuran solution containing a boron trifluoride/tetrahydrofuran complex dropwise over a period of about 2 hours. The internal temperature of the reaction mixture during the dropwise addition was kept at 35-50° C. Upon completion of the dropwise addition, the obtained mixture was heated for about 3 hours at 50° C. The reacted mixture was cooled in an ice water bath, and then 20 mL of acetone, 50 mL of water and 50 mL of 5 wt % hydrochloric acid water were added dropwise in that order. The obtained mixture was extracted 3 times with 50 mL of toluene and the organic layers were combined. The obtained organic layer was washed once with 50 mL of 5 wt % hydrochloric acid water and then twice with 50 mL of brine. After dehydration treatment of the obtained organic layer with anhydrous magnesium sulfate, the organic layer was concentrated under reduced pressure to obtain 41.9 g of an oil containing trans-[8-chloro-11-(nitromethyl)-10,11-dihydrodibenzo[b,f]oxepin-10-yl]methanol.

Composition: trans-form: 88.0%; cis-form: 11.5%.

$^1$H-NMR data for trans-[8-chloro-11-(nitromethyl)-10,11-dihydrodibenzo[b,f]oxepin-10-yl]methanol (δppm, CDCl$_3$): 3.27-3.31 (1H, m), 3.40 (1H, t-like, J=ca. 8 Hz), 3.53-3.69 (1H, m), 4.12-4.18 (1H, m), 4.63 (1H, dd, J=12.8 Hz), 4.77 (1H, dd, J=12.8 Hz), 7.08-7.31 (7H, m).

Example 2

Synthesis of trans-[8-chloro-11-(nitromethyl)-10,11-dihydrodibenzo[b,f]oxepin-10-yl]methyl methanesulfonate (compound (IV), Y=methanesulfonyl) (step B)

A mixture of 41.9 g of the oil containing trans-[8-chloro-11-(nitromethyl)-10,11-dihydrodibenzo[b,f]oxepin-10-yl]methanol obtained in Example 1, 150 mL of toluene and 30.9 g (305 mmol) of triethylamine was cooled to 0-10° C. To this there was added dropwise 16.8 g (146 mmol) of methanesulfonyl chloride over a period of about 30 minutes. The obtained mixture was stirred at 0-10° C. over a period of about 3 hours. After adding 150 mL of water to the reacted mixture, it was stirred at room temperature for 30 minutes and then liquid separation was performed to obtain an organic layer. The aqueous layer was extracted twice with 50 mL of toluene and the obtained organic layer was combined with the previously obtained organic layer. The obtained organic layer was washed with 100 mL of approximately 3 wt % hydrochloric acid water, with 50 mL of 5 wt % sodium bicarbonate water and with 50 mL of brine. After dehydration treatment of the obtained organic layer with anhydrous magnesium sulfate, the treated organic layer was concentrated to obtain approximately 52 g of an oil containing trans-[8-chloro-11-(nitromethyl)-10,11-dihydrodibenzo[b,f]oxepin-10-yl]methyl methanesulfonate.

Composition: trans-form: 88.4%; cis-form: 6.5%.

$^1$H-NMR data for trans-[8-chloro-11-(nitromethyl)-10,11-dihydrodibenzo[b,f]oxepin-10-yl]methyl methanesulfonate (δppm, CDCl$_3$): 2.93 (3H, s), 3.59 (1H, m), 3.93 (1H, t, J=10 Hz), 4.11 (1H, m), 4.27 (1H, dd, J=10.6 Hz).

Example 3

Synthesis of trans-5-chloro-2,3,3a,12b-tetrahydro-1H-dibenzo[2,3;6,7]-oxepino[4,5-c]pyrrole (compound (V)) (step C)

Into a 1000 mL volume autoclave reactor there were charged the total amount (approximately 52 g) of the oil containing trans-[8-chloro-11-(nitromethyl)-10,11-dihydrodibenzo[b,f]oxepin-10-yl]methyl methanesulfonate obtained in Example 2, 200 mL of methanol, 50 mL of tetrahydrofuran and 14.6 g (244 mmol) of acetic acid, and approximately 7 g of sponge nickel (PL-9T by Kawaken Fine Chemicals Co., Ltd., Lot No. 1057, wet product) was added. After replacing the gas phase with a hydrogen atmosphere, the mixture was stirred for approximately 13 hours at 40-50° C. The hydrogen pressure during the reaction was approximately 0.8 Mpa. The reacted mixture was cooled to room temperature and then the hydrogen was purged and the catalyst was filtered. When the obtained solution was analyzed with a liquid chromatography mass spectrometer, approximately 18% residue of compound (V') (Y=methanesulfonyloxy group) was found.

LC/MS (ESI) m/e: 368 (M+H)$^+$.

To this solution there was added 10.0 g (72.4 mmol) of potassium carbonate powder and the obtained mixture was stirred for approximately 10 hours at 50° C. The reacted mixture was partially concentrated, 100 mL of water and 100 mL of toluene were added to the obtained mixture, ammonia water was used to adjust the pH of the aqueous layer to 12, and liquid separation was performed to obtain an organic layer. The aqueous layer was extracted twice with 100 mL of toluene and the obtained organic layer was combined with the previously obtained organic layer. The obtained organic layer was washed twice with 100 mL of water. The obtained organic layer was subjected to dehydration treatment with anhydrous magnesium sulfate, and the treated organic layer was concentrated to obtain 34.0 g of an oil containing trans-5-chloro-2,3,3a,12b-tetrahydro-1H-dibenzo[2,3;6,7]-oxepino[4,5-c]pyrrole.

Composition: trans-form: 76.3%; cis-form: 5.4%.

A mixture of 18.5 g of the oil containing trans-5-chloro-2,3,3a,12b-tetrahydro-1H-dibenzo[2,3;6,7]-oxepino[4,5-c]pyrrole and 66 mL of tert-butyl methyl ether was heated to 50-55° C., and then 11.44 g (73.0 mmol) of 4-chlorobenzoic acid was added to obtain a homogeneous solution. The solution was cooled to 0-5° C. over a period of 2 hours, and stirred for 1 hour at the same temperature. The precipitated crystals in the obtained mixture were separated off by filtration, and the crystals were rinsed with 10 mL of tert-butyl methyl ether and dried to obtain 20.0 g of gray crystals. The crystals were added to a mixture of 50 mL of water and 50 mL of toluene, a 20 wt % sodium hydroxide aqueous solution was used to adjust the pH of the aqueous layer to 12, and then liquid separation was performed to obtain an organic layer. The aqueous layer was extracted twice with 50 mL of toluene and the obtained organic layer was combined with the previously obtained organic layer. The obtained organic layer was washed 3 times with 30 mL of brine. The obtained organic layer was subjected to dehydration treatment with anhydrous magnesium sulfate, and the treated organic layer was concentrated to obtain 9.45 g of a solid containing trans-5-chloro-2,3,3a,12b-tetrahydro-1H-dibenzo[2,3;6,7]-oxepino[4,5-c]pyrrole. The portable yields in Reference Example 1 and Examples 1-3 were 50% (based on trans-form).

Composition: trans-form: 94.5%; cis-form: 1.0%.

$^1$H-NMR data for trans-5-chloro-2,3,3a,12b-tetrahydro-1H-dibenzo[2,3;6,7]-oxepino[4,5-c]pyrrole (δppm, CDCl$_3$): 3.32-3.33 (2H, m), 3.45-3.51 (2H, m), 3.59-3.66 (2H, m), 7.06-7.23 (7H, m).

Example 4

Synthesis of trans-5-chloro-2,3,3a,12b-tetrahydro-2-methyl-1H-dibenzo[2,3;6,7]-oxepino[4,5-c]pyrrole (compound (VI)) (step D)

A mixture of 5.66 g (69.9 mmol) of a 37 wt % formaldehyde aqueous solution, 4.82 g (104 mmol) of formic acid and (10 mL) of toluene was heated to 65-70° C., and then a mixture of 9.49 g of the solid containing trans-5-chloro-2,3,3a,12b-tetrahydro-1H-dibenzo[2,3;6,7]-oxepino[4,5-c]pyrrole obtained in Example 3 and 25 mL of toluene was added dropwise over a period of 15 minutes. Upon completion of the dropwise addition, the obtained mixture was stirred for 1 hour at the same temperature. The reacted mixture was cooled to room temperature, 20 mL of toluene and 20 mL of water were added thereto, a 20 wt % sodium hydroxide aqueous solution was used to adjust the pH of the aqueous layer to above 12, and then liquid separation was performed to obtain an organic layer. The aqueous layer was extracted twice with 25 mL of toluene and the obtained organic layer was combined with the previously obtained organic layer. The obtained organic layer was washed twice with 25 mL of brine. The obtained organic layer was subjected to dehydration treatment with anhydrous magnesium sulfate, and the treated organic layer was concentrated to obtain 9.52 g of a solid containing trans-5-chloro-2,3,3a,12b-tetrahydro-2-methyl-1H-dibenzo[2,3;6,7]-oxepino[4,5-c]pyrrole. The apparent yield was 95%.

Composition: trans-form: 93.6%; cis-form: 1.3%.

$^1$H-NMR data for trans-5-chloro-2,3,3a,12b-tetrahydro-2-methyl-1H-dibenzo[2,3;6,7]-oxepino[4,5-c]pyrrole (δppm, CDCl$_3$): 2.56 (3H, s), 3.10-3.20 (2H, m), 3.21-3.26 (2H, m), 3.62-3.66 (2H, m), 7.07-7.27 (7H, m).

Production Example 1

Synthesis of trans-5-chloro-2,3,3a,12b-tetrahydro-2-methyl-1H-dibenzo[2,3;6,7]-oxepino[4,5-c]pyrrole maleate A mixture of 9.52 g of the solid containing trans-5-chloro-2,3,3a,12b-tetrahydro-2-methyl-1H-dibenzo[2,3;6,7]-oxepino[4,5-c]pyrrole obtained in Example 4 and 25 mL of ethanol was heated to 60° C., and then 4.25 g (36.6 mmol) of maleic acid was added to obtain a homogeneous solution. Approximately 0.2 g of active carbon (SEISEI SHIRASAGI, product of Takeda Pharmaceutical Co., Ltd.) was added to the solution and the mixture was stirred at the same temperature for 25 minutes. The mixture was filtered at the same temperature to obtain a filtrate. The filtered active carbon was washed with 10 mL of ethanol and the obtained wash solution was combined with the previously obtained filtrate. The obtained solution was cooled to 40° C., and trans-5-chloro-2,3,3a,12b-tetrahydro-2-methyl-1H-dibenzo[2,3;6,7]-oxepino[4,5-c]pyrrole maleate seed crystals were added. The obtained mixture was cooled to 0-5° C. and then stirred for 2 hours. The precipitated crystals were separated off by filtration, and the crystals were washed with approximately 10 mL of cold ethanol and dried to obtain 7.87 g of trans-5-chloro-2,3,3a,12b-tetrahydro-2-methyl-1H-dibenzo[2,3;6,7]-oxepino[4,5-c]pyrrole maleate as a white solid. The yield was 63% (based on trans-form).

Composition: trans-form: 99.5%; cis-form: <0.1%.

Reference Example 2

Synthesis of 2-(2-(4-chlorophenoxy)phenyl)acetic acid

A mixture of 552.0 g (4.0 mol) of potassium carbonate and 1500 mL of diglyme was kept at 0-20° C. while adding 283.1 g (2.2 mol) of 4-chlorophenol thereto and mixing, and then 5.74 g (0.04 mol) of copper(I) bromide was added. The obtained mixture was heated to 100° C., and 90.3 g (0.53 mol) of 2-chlorophenylacetic acid was added. This mixture was stirred at the same temperature for 1 hour, and then 159.4 g (0.93 mol) of 2-chlorophenylacetic acid was further added. After stirring the obtained mixture at 120-130° C. for approximately 8 hours, completion of the reaction was confirmed by high-performance liquid chromatography. The reacted mixture was cooled to near room temperature, and then approximately 700 mL of water and approximately 650 mL of 35 wt % hydrochloric acid water were added in that order. The pH of the aqueous layer was below 1. After further adding about 500 mL of water to the obtained mixture, it was extracted once with 400 mL and once with 200 mL of toluene, in that order. The obtained organic layers were combined and washed 3 times with 500 mL of water and once with 500 mL of brine, in that order. The obtained organic layer was subjected to dehydration treatment with anhydrous magnesium sulfate, and 100 mL of heptane was added dropwise to approximately 400 g of the residue obtained by partially concentrating the treated organic layer. The internal temperature of the mixture after the dropwise addition was about 70° C., and crystals precipitated in the mixture. Upon completion of the dropwise addition, the mixture was cooled to 20-25° C. and the crystals were separated off by filtration. The obtained crystals were washed with 100 mL of a heptane/toluene=1/1 mixed solvent and dried under reduced pressure to obtain 245.6 g of 2-(2-(4-chlorophenoxy)phenyl)acetic acid as a white solid. The yield was 68.8%.

Reference Example 3

Synthesis of ethyl 2-(2-(4-chlorophenoxy)phenyl)acetate

After mixing 259.1 g of potassium carbonate (1.88 mol, granular reagent), 985 mL of tert-butyl methyl ether, 493 mL of N,N-dimethylformamide and 202.4 g (1.31 mol) of diethyl sulfate, a mixture of 328.4 g (1.25 mol) of 2-(2-(4-chlorophenoxy)phenyl)acetic acid and 164 mL of N,N-dimethylformamide was added dropwise to the obtained mixture over a period of one hour. The internal temperature of the mixture during the dropwise addition was 25-40° C. Upon completion of the dropwise addition, the obtained mixture was stirred at 25° C. for 12 hours, and completion of the reaction was confirmed by high-performance liquid chromatography. A 1642 mL portion of water was slowly added dropwise to suspend the reaction. The internal temperature of the mixture during the dropwise addition was 25-35° C. The obtained mixture was subjected to liquid separation, and after washing the organic layer with 656 mL of water and 495 mL of brine in that order, the obtained organic layer was subjected to dehydration treatment with anhydrous magnesium sulfate and the treated organic layer was concentrated to obtain 366.4 g of crude ethyl 2-(2-(4-chlorophenoxy)phenyl)acetate as an oil.

Reference Example 4

Synthesis of ethyl 2-(2-(4-chlorophenoxy)phenyl)-3-hydroxyacrylate ester

After mixing 62.5 g of 60 wt % sodium hydride (1.56 mol, oil mixture) and 1280 mL of tetrahydrofuran, 5.75 g (0.125 mol) of absolute ethanol was added dropwise thereto. The internal temperature of the mixture during the dropwise addition was 23° C. A mixed solution comprising 366.4 g of the crude ethyl 2-(2-(4-chlorophenoxy)phenyl)acetate obtained in Reference Example 3, 208.4 g (2.81 mol) of ethyl formate and 366 mL of tetrahydrofuran was added dropwise thereto over a period of 1.5 hours. The internal temperature of the mixture during the dropwise addition was 15-25° C. After stirring the obtained mixture at the same temperature for approximately 2.5 hours, completion of the reaction was confirmed by high-performance liquid chromatography. The obtained mixture was slowly added dropwise to and mixed with a mixed solution containing 163 g (1.56 mol) of 35 wt % hydrochloric acid and 363 mL of water. The obtained mixture was subjected to liquid separation, the aqueous layer was extracted with 366 mL of toluene, and the obtained organic layers were combined. After washing the organic layer with 366 mL of brine, it was concentrated to obtain 421 g of crude ethyl 2-(2-(4-chlorophenoxy)phenyl)-3-hydroxyacrylate ester as an oil.

Reference Example 5

Synthesis of ethyl (E)-2-chlorodibenzo[b,f]oxepin-10-carboxylate

After mixing 421 g of the crude ethyl 2-(2-(4-chlorophenoxy)phenyl)-3-hydroxyacrylate ester obtained in Reference Example 4 with 1500 g of pyrophosphoric acid, the obtained mixture was stirred at 65° C.-74° C. for approximately 12 hours and completion of the reaction was confirmed by high-performance liquid chromatography. The obtained mixture was slowly poured into and mixed with a mixture of 1500 mL of ice water and 730 mL of ethyl acetate. The obtained mixture was subjected to liquid separation at 40-50° C., the aqueous layer was extracted with 370 mL of ethyl acetate, and the obtained organic layers were combined. The organic layer was washed once with 360 mL of brine, once with 360 mL of 10 wt % aqueous sodium carbonate and twice with 360 mL of brine, in that order. The washings were carried out at 40-50° C. The obtained organic layer was subjected to dehydration treatment with anhydrous magnesium sulfate, and the treated organic layer was concentrated to obtain approximately 399 g of an oil. The oil was mixed with 420 mL of 2-propanol, and the obtained mixture was slowly cooled from 40° C. to 5° C. while stirring and then kept at 0-5° C. for about 1 hour. The precipitated crystals were separated off by filtration and washed with 50 mL of 2-propanol and dried to obtain 199.2 g of ethyl (E)-2-chlorodibenzo[b,f]oxepin-10-carboxylate as a white solid. The portable yields for Reference Examples 3-5 were 53.0%.

$^1$H-NMR data for ethyl(E)-2-chlorodibenzo[b,f]oxepin-10-carboxylate (δppm, CDCl$_3$): 1.40 (3H, t, J=7 Hz), 4.39 (2H, q, J=7 Hz), 7.14-7.40 (6H, m), 7.51 (1H, dd, J=7.1 Hz), 7.79 (1H, s).

Reference Example 6

Synthesis of ethyl trans-2-chloro-11-(nitromethyl)-10,11-dihydrodibenzo[b,f]oxepin-10-carboxylate (compound (II), R=ethyl)

After mixing 190.8 g (0.634 mol) of the ethyl (E)-2-chlorodibenzo[b,f]oxepin-10-carboxylate obtained in Reference Example 5 with 387.2 g (6.34 mol) of nitromethane, 38.8 g (0.254 mol) of 1,8-diazobicyclo[5.4.0]-7-undecene was added dropwise thereto in 4 portions over a period of approximately 5 hours. The internal temperature of the mixture during the dropwise addition was 19-27° C. After further stirring the obtained mixture at 25° C. for approximately 13 hours, completion of the reaction was confirmed by high-performance liquid chromatography. A mixed solution comprising 33.1 g of 35 wt % hydrochloric acid and 381 mL of water was added dropwise to the obtained mixture. The internal temperature of the mixture during the dropwise addition was 15-20° C. To the obtained mixture there were added 1360 mL of methyl isobutyl ketone, 400 mL of water and 100 mL of methanol, the mixture was stirred, and liquid separation was performed. The obtained organic layer was washed twice with 300 mL of a methanol/water=1/10 (v/v) mixed solution and once with 200 mL of 5 wt % brine, in that order. The obtained organic layer was subjected to dehydration treatment with anhydrous magnesium sulfate, and upon analysis of the treated organic layer by high-performance liquid chromatography, the product ratio for ethyl 2-chloro-11-(nitromethyl)-10,11-dihydrodibenzo[b,f]oxepin-10-carboxylate was found to be trans/cis=86/14. The organic layer was concentrated to a total amount of approximately 383 g, and the obtained concentrated residue was cooled from 57° C. to 11° C. over a period of approximately 24 hours. The precipitated crystals were separated off by filtration, and the crystals were washed with 100 mL of a heptane/methyl isobutyl ketone=4/1 mixed solution and dried to obtain 160.5 g of ethyl trans-2-chloro-11-(nitromethyl)-10,11-dihydrodibenzo[b,f]oxepin-10-carboxylate as whitish crystals.

Composition: trans-form: 99.3%; cis-form: 0.7%.

The mother liquor obtained by this filtration was combined with the previous solution, and upon analysis of the obtained mixture by high-performance liquid chromatography, the ratio for ethyl 2-chloro-11-(nitromethyl)-10,11-dihydrodibenzo[b,f]oxepin-10-carboxylate was found to be trans/cis=55/45. After adding 5.0 g (0.033 mol) of 1,8-diazobicyclo [5.4.0]-7-undecene to the mixture, the resulting mixture was stirred at 55° C. for approximately 1 hour and 30 minutes. The mixture was cooled to room temperature, and then washed once with a mixture of 50 mL of 10 wt % hydrochloric acid and 90 mL of water, twice with 90 mL of water and once with 90 mL of brine, in that order. The obtained organic layer was subjected to dehydration treatment with anhydrous magnesium sulfate, and upon analysis of the treated organic layer by high-performance liquid chromatography, the trans/cis ratio for the ethyl 2-chloro-11-(nitromethyl)-10,11-dihydrodibenzo[b,f]oxepin-10-carboxylate was 85/15. The organic layer was concentrated to a total amount of approximately 115 g, and the obtained concentrated residue was cooled from 55° C. to 7° C. over a period of approximately 24 hours. The precipitated crystals were separated off by filtration, and the crystals were washed with 30 mL of a heptane/methyl isobutyl ketone=4/1 mixed solution and dried to obtain 34.0 g of ethyl trans-2-chloro-11-(nitromethyl)-10,11-dihydrodibenzo[b,f]oxepin-10-carboxylate as light yellow crystals. The total yield of the two crystal separating procedures was 84.6%.

Composition: trans-form: 99.3%; cis-form: 0.7%.

$^1$H-NMR data for ethyl trans-2-chloro-11-(nitromethyl)-10,11-dihydrodibenzo[b,f]oxepin-10-carboxylate (δppm, CDCl$_3$): 1.06 (3H, t, J=7 Hz), 4.05 (2H, q, J=7 Hz), 4.09 (1H, d-like, J=4 Hz), 4.377-4.45 (2H, m), 4.55-4.60 (1H, m), 7.11-7.36 (7H, m).

Example 5

Synthesis of trans-[2-chloro-11-(nitromethyl)-10,11-dihydrodibenzo[b,f]oxepin-10-yl]methanol (compound (III)) (step A)

A 180.9 g portion of the ethyl trans-2-chloro-11-(nitromethyl)-10,11-dihydrodibenzo[b,f]oxepin-10-carboxylate obtained in Reference Example 6 (mixture of the initially obtained whitish crystals and subsequently obtained light yellow crystals, 0.5 mol, trans/cis=99.3/0.7) was added to and mixed with a mixture of 904 mL of tetrahydrofuran and 24.6 g of sodium borohydride (0.65 mol, powdered). Next, 134.1 g (45.5 wt %, 0.90 mol) of a boron trifluoride/tetrahydrofuran complex was added dropwise to the obtained mixture under a nitrogen atmosphere, over a period of about 1 hour and 30 minutes. The internal temperature of the mixture during the dropwise addition was 20-26° C. The obtained mixture was stirred at the same temperature for approximately 2 hours, and then stirred at 40° C. for approximately 3 hours. After cooling the reaction mixture with an ice water bath, 58 g of acetone and 452 mL of water were added dropwise in that order, at an internal temperature of 5-10° C. To the obtained mixture there were added 542 mL of toluene and 180 mL of methanol, the mixture was stirred, and liquid separation was performed. The obtained organic layer was washed twice with 250 mL of a methanol/water=1/10 (v/v) mixed solution and once with 300 mL of 10 wt % brine in that order, and then the organic layer was subjected to dehydration treatment with anhydrous magnesium sulfate and concentrated to obtain 158.1 g of crude trans-[2-chloro-11-(nitromethyl)-10,11-dihydrodibenzo[b,f]oxepin-10-yl]methanol as a highly viscous fluid.

Composition: trans-form: 99.6%; cis-form: 0.4%.

$^1$H-NMR data for trans-[2-chloro-11-(nitromethyl)-10,11-dihydrodibenzo[b,f]oxepin-10-yl]methanol (δppm, CDCl$_3$): 3.20-3.35 (1H, m), 3.40 (1H, broad t, J=ca. 10 Hz), 3.71 (1H, dd, J=10.5), 4.13 (1H, ddd, J=8, 7.4 Hz), 4.60 (1H, dd, J=13.7 Hz), 4.76 (1H, dd, J=13.8 Hz), 7.05-7.28 (7H, m).

Example 6

Synthesis of trans-[2-chloro-11-(nitromethyl)-10,11-dihydrodibenzo[b,f]oxepin-10-yl]methyl methanesulfonate (compound (IV), Y=methanesulfonyl) (step B)

To a mixture of 158.0 g of the crude trans-[2-chloro-11-(nitromethyl)-10,11-dihydrodibenzo[b,f]oxepin-10-yl]methanol obtained in Example 5 and 1272 mL of toluene there was added 101.2 g (1.0 mol) of triethylamine, and after mixing, 63.0 g (0.55 mol) of methanesulfonyl chloride was added dropwise over a period of about 1 hour and 30 minutes. The internal temperature of the mixture during the dropwise addition was 10-20° C. After stirring the obtained mixture at the same temperature for approximately 1 hour, completion of the reaction was confirmed by high-performance liquid chromatography. To the obtained reaction mixture there was added dropwise a mixed solution comprising 41.8 g of 35 wt % hydrochloric acid and 940 mL of water, and after mixing, liquid separation was performed. The obtained organic layer was washed twice with 320 mL of water to obtain 1385 g of a toluene solution containing trans-[2-chloro-11-(nitromethyl)-10,11-dihydrodibenzo[b,f]oxepin-10-yl]methyl methanesulfonate. Analysis by the high-performance liquid chromatographic internal standard method showed that 190.0 g of trans-[2-chloro-11-(nitromethyl)-10,11-dihydrodibenzo[b,f]oxepin-10-yl]methyl methanesulfonate was present in the solution. The portable yields for Examples 5 and 6 were 95.5%.

$^1$H-NMR data for trans-[2-chloro-11-(nitromethyl)-10,11-dihydrodibenzo[b,f]oxepin-10-yl]methyl methanesulfonate (δppm, CDCl$_3$): 3.62 (1H, m), 3.91 (1H, broad t, J=ca. 10 Hz), 4.07 (1H, ddd, J=7, 7.4 Hz), 4.33 (1H, dd, J=10.5 Hz), 4.58 (1H, dd, J=13.7 Hz), 4.75 (1H, dd, J=13.7 Hz), 7.10-7.33 (7H, m).

Example 7

Synthesis of trans-5-chloro-2,3,3a,12b-tetrahydro-1H-dibenzo[2,3;6,7]-oxepino[4,5-c]pyrrole (compound (V)) (step C)

A 1240 g portion of a toluene solution containing the trans-[2-chloro-11-(nitromethyl)-10,11-dihydrodibenzo[b,f]oxepin-10-yl]methyl methanesulfonate obtained in Example 6 (content: 170.0 g, 0.427 mol) was concentrated to approximately 699 g. After charging the obtained concentrated residue, approximately 750 mL of 2-propanol and approximately 20 g of developed nickel (PL-9T by Kawaken Fine Chemicals Co., Ltd., (wet product)) into a 1000 mL volume autoclave reactor, the gas phase was replaced with a hydrogen atmosphere and the mixture was stirred at 50-67° C. for about 20 hours. The hydrogen pressure during the reaction was approximately 0.6 Mpa. After filtering the solid in the reaction mixture, the obtained filtrate was mixed with 130 mL of a 10 wt % sodium hydroxide aqueous solution and the mixture was stirred at 25-40° C. for about 1 hour. To the obtained mixture there was added approximately 285 mL of a 10 wt % sodium hydroxide aqueous solution until the pH of the mixture reached 14, and the 2-propanol was distilled off under reduced pressure. The obtained concentrated residue was subjected to liquid separation and then the aqueous layer was extracted with toluene. The obtained organic layers were combined to obtain approximately 1449 g of a solution containing trans-5-chloro-2,3,3a,12b-tetrahydro-1H-dibenzo[2,3;6,7]-oxepino[4,5-c]pyrrole. Upon analysis of the solution by high-performance liquid chromatography, the trans-5-chloro-2,3,3a,12b-tetrahydro-1H-dibenzo[2,3;6,7]-oxepino[4,5-c]pyrrole content was found to be 91.2 g, for a yield of 78%.

Composition: trans-form: 98.3%; cis-form: 1.7%.

Example 8

Synthesis of trans-5-chloro-2,3,3a,12b-tetrahydro-2-methyl-1H-dibenzo[2,3;6,7]-oxepino[4,5-c]pyrrole (compound (VI)) (step D)

The total amount of the solution containing trans-5-chloro-2,3,3a,12b-tetrahydro-1H-dibenzo[2,3;6,7]-oxepino[4,5-c]

pyrrole obtained in Example 7 (content: 91.2 g, 0.335 mol) was concentrated under reduced pressure to approximately 700 mL. After then adding 54.3 g (0.67 mol) of a 37 wt % formaldehyde aqueous solution and 52.6 g (1.00 mol) of 88 wt % formic acid, the obtained mixture was stirred at 60° C. for 2 hours. Upon completion of the reaction, the obtained mixture was cooled to room temperature, and 400 g of a 10 wt % sodium hydroxide aqueous solution was added thereto for liquid separation. The aqueous layer was extracted with 100 mL of toluene and the obtained organic layers were combined. The organic layer was washed with a mixture of 200 mL of water and 50 mL of methanol, and then with 200 mL of brine. The obtained organic layer was subjected to dehydration treatment with anhydrous sodium sulfate, and the treated organic layer was concentrated to obtain 296 g of a solid containing trans-5-chloro-2,3,3a,12b-tetrahydro-2-methyl-1H-dibenzo[2,3;6,7]-oxepino[4,5-c]pyrrole.

Production Example 2

Purification of trans-5-chloro-2,3,3a,12b-tetrahydro-2-methyl-1H-dibenzo[2,3;6,7]-oxepino[4,5-c]pyrrole The total amount of the solid containing trans-5-chloro-2,3,3a,12b-tetrahydro-2-methyl-1H-dibenzo[2,3;6,7]-oxepino[4,5-c]pyrrole obtained in Example 8 was dissolved in 700 mL of ethyl acetate, and then 39.2 g (0.436 mol) of oxalic acid was added and the obtained mixture was heated at approximately 60° C. for about 1 hour and then cooled to 25° C. The precipitated crystals were separated off by filtration and washed with ethyl acetate. The obtained crystals were added to a mixture of 400 mL of a 10 wt % sodium hydroxide aqueous solution and 500 mL of toluene, and the mixture was stirred. After liquid separation of the obtained mixture, the aqueous layer was extracted once with 200 mL and once with 100 mL of toluene and the obtained organic layers were combined and then washed twice with 200 mL of water and once with 200 mL of brine. The obtained organic layer was subjected to dehydration treatment with anhydrous magnesium sulfate and concentrated to obtain 91.7 g of purified trans-5-chloro-2,3,3a,12b-tetrahydro-2-methyl-1H-dibenzo[2,3;6,7]-oxepino[4,5-c]pyrrole as a high-viscosity oil. The portable yields for Examples 8 and Production Example 2 were 95.8%.
Composition: trans-form: 96.6%; cis-form: 1.5%.

Production Example 3

Synthesis of trans-5-chloro-2,3,3a,12b-tetrahydro-2-methyl-1H-dibenzo[2,3;6,7]-oxepino[4,5-c]pyrrole maleate To 91.0 g (0.32 mmol) of the purified trans-5-chloro-2,3,3a,12b-tetrahydro-2-methyl-1H-dibenzo[2,3;6,7]-oxepino[4,5-c]pyrrole obtained in Production Example 2 there were added 310 mL of 99.5% ethanol and 40.6 g (0.35 mol) of maleic acid, and the obtained mixture was heated to 60° C. to obtain a homogeneous solution. The solution was cooled to −10° C. over a period of 18 hours. The precipitated crystals were separated off by filtration, and the crystals were washed with 45 mL of cold ethanol and dried to obtain 108.2 g of trans-5-chloro-2,3,3a,12b-tetrahydro-2-methyl-1H-dibenzo[2,3;6,7]-oxepino[4,5-c]pyrrole maleate as a white solid. The yield was 84.6%.
Composition: trans-form: 100.0%; cis-form: 0%.

INDUSTRIAL APPLICABILITY

Maleic acid salts of trans-dibenzoxenopyrrole compounds are useful as therapeutic agents for ataxia, for example (see Japanese Patent Public Inspection No. 2006-527238), and the process and compounds of the invention can be utilized for production of such compounds.

The invention claimed is:

1. A process for production of a trans-dibenzoxenopyrrole compound represented by general formula (VI):

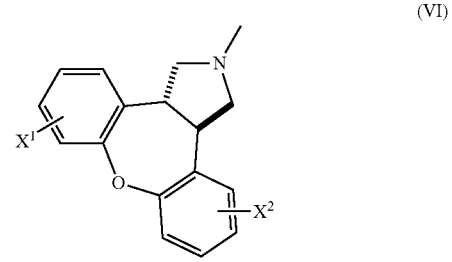

wherein $X^1$ and $X^2$ are the same or different and each independently represents hydrogen or a halogen atom, or a pharmacologically acceptable salt thereof, the process comprising the following steps A-D:

Step A: A step in which a compound represented by general formula (II):

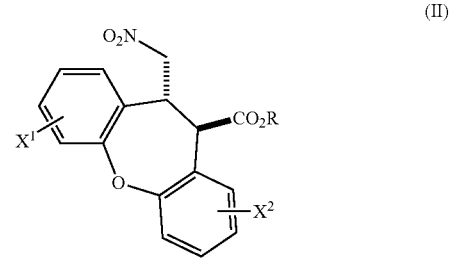

wherein R represents an alkyl group optionally substituted with a phenyl group, and $X^1$ and $X^2$ have the same definitions as above;

is reduced to obtain a compound represented by general formula (III):

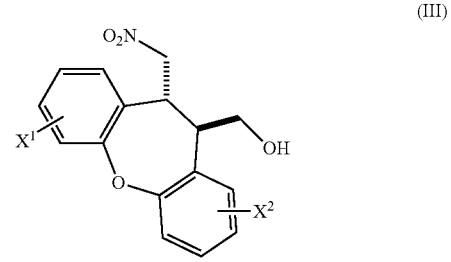

wherein $X^1$ and $X^2$ have the same definitions as above;

Step B: A step of leaving group conversion of a compound represented by general formula (III) to obtain a compound represented by general formula (IV):

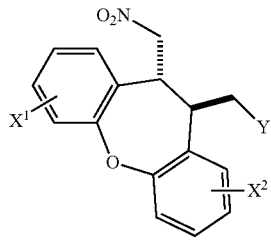

(IV)

wherein X¹ and X² have the same definitions as above, and Y represents a leaving group;

Step C: A step in which a compound represented by general formula (IV) is subjected to hydrogenation to obtain a trans-dibenzoxenopyrrole compound represented by general formula (V):

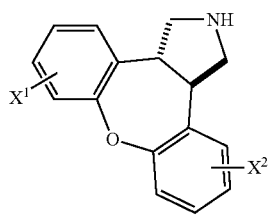

(V)

wherein X¹ and X² have the same definitions as above; and

Step D: A step in which a trans-dibenzoxenopyrrole compound represented by general formula (V) is methylated to obtain a trans-dibenzoxenopyrrole compound represented by general formula (VI).

2. A process for production of a trans-dibenzoxenopyrrole compound represented by general formula (VI):

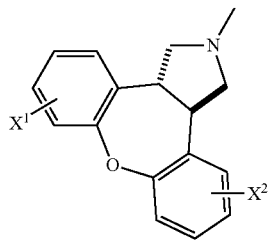

(VI)

wherein X¹ and X² are the same or different and each independently represents hydrogen or a halogen atom, the process comprising a step in which a trans-dibenzoxenopyrrole compound represented by general formula (V):

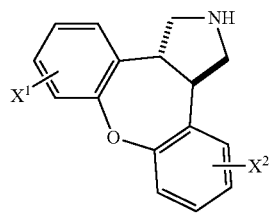

(V)

wherein X¹ and X² are the same or different and each independently represents hydrogen or a halogen atom, is methylated to obtain a trans-dibenzoxenopyrrole compound represented by general formula (VI).

3. The process according to claim 1, wherein the reduction of the compound represented by general formula (II) is carried out using a boron hydride compound.

4. The process according to claim 1, wherein the reduction of the compound represented by general formula (II) is carried out using borane.

5. The process according to claim 1, wherein the reduction of the compound represented by general formula (II) is carried out using sodium borohydride.

6. The process according to claim 5, wherein the reduction of the compound represented by general formula (II) is carried out also using boron trifluoride, sulfuric acid or dimethyl sulfate.

7. The process according to claim 1, wherein the leaving group conversion of the compound represented by general formula (III) is accomplished using a halogenating agent or sulfonating agent.

8. The process according to claim 1, wherein the leaving group conversion of the compound represented by general formula (III) is accomplished using a C1-6 alkanesulfonyl chloride.

9. The process according to claim 1, wherein the leaving group conversion of the compound represented by general formula (III) is accomplished using methanesulfonyl chloride.

10. The process according to claim 1, wherein the methylation of the trans-dibenzoxenopyrrole compound represented by general formula (V) is accomplished using formaldehyde.

11. The process according to claim 10, wherein the methylation of the trans-dibenzoxenopyrrole compound represented by general formula (V) is accomplished also using formic acid.

* * * * *